United States Patent [19]

Nick et al.

[11] Patent Number: 4,711,781

[45] Date of Patent: * Dec. 8, 1987

[54] MEDICINAL SELF-ADHESIVE PLASTER

[76] Inventors: Erich Nick, Eichhörnchenweg 2, D-2080 Pinneberg; Günter Guse, Lilicronstr. 30, D-2000 Hamburg 73; Bodo Asmussen, Dorotheenweg 1a, D-2071 Ammerbek 2, all of Fed. Rep. of Germany

[*] Notice: The portion of the term of this patent subsequent to Dec. 8, 2004 has been disclaimed.

[21] Appl. No.: 745,170

[22] Filed: Jun. 17, 1985

[30] Foreign Application Priority Data

Jun. 23, 1984 [DE] Fed. Rep. of Germany ....... 3423293

[51] Int. Cl.[4] ..................... A61L 15/03; A61L 15/06; A61F 13/02; A61K 31/505
[52] U.S. Cl. ..................... 424/446; 424/449; 604/896; 604/897; 604/307; 128/156; 428/355
[58] Field of Search ............ 424/16, 19, 20, 21, 424/26, 27, 28, 78, 83, 443, 446, 449; 604/897, 896, 304, 307; 128/156; 156/289, 327, 332, 334; 428/355, 356

[56] References Cited

U.S. PATENT DOCUMENTS

| 3,438,371 | 4/1969 | Fischer et al. | 128/156 |
| 4,297,995 | 11/1981 | Golub | 604/897 |
| 4,564,010 | 1/1986 | Coughlan et al. | 604/896 |
| 4,568,343 | 2/1986 | Leeper et al. | 604/897 |

FOREIGN PATENT DOCUMENTS

| 67208 | 12/1914 | Austria . | |
| 13606 | 7/1980 | European Pat. Off. . | |
| 1755526 | 8/1957 | Fed. Rep. of Germany . | |
| 2604718 | 8/1976 | Fed. Rep. of Germany . | |
| 3119752 | 1/1982 | Fed. Rep. of Germany . | |
| 3111734 | 1/1982 | Fed. Rep. of Germany . | |
| 3208853 | 9/1982 | Fed. Rep. of Germany . | |
| 3202775 | 3/1983 | Fed. Rep. of Germany | 424/28 |
| 3231400 | 3/1983 | Fed. Rep. of Germany . | |
| 55-160716 | 12/1980 | Japan . | |
| 338554 | 5/1959 | Switzerland . | |
| 341948 | 10/1959 | Switzerland . | |
| 2100605 | 1/1983 | United Kingdom . | |

Primary Examiner—John Kight
Assistant Examiner—Nathan M. Nutter
Attorney, Agent, or Firm—John C. Smith, Jr.

[57] ABSTRACT

A self-adhesive medicinal plaster comprises a continuous adhesive coating on one surface of a carrier web, a plurality of non-permeable, separating film elements spaced from each other on the surface of the adhesive coating and a plurality of active ingredient elements containing a medication, each disposed on the surface of one of the separating film elements whereby the medicated active ingredient composition is isolated from the adhesive composition.

22 Claims, 2 Drawing Figures

MEDICINAL SELF-ADHESIVE PLASTER

FIELD OF THE INVENTION

This invention relates to a medicinal self-adhesive plaster with active ingredient elements spaced from each other on a carrier coated with adhesive for transdermal application.

BACKGROUND OF THE INVENTION

German Offenlegungsschrift No. 3,202,775 describes an adhesive plaster in which medicinal active ingredient elements are applied directly to an adhesive layer. The adhesive is on a carrier, and the entire system is protected with a releasable cover which is pulled off before use.

Although such as plaster can be produced economically, it has serious disadvantages which render it unsatisfactory in practice. On the one hand, because of interaction, inherent to the system, between the adhesive and the active ingredient, it is necessary both to adapt the adhesive to the formulation of the active ingredient and on the other hand to adapt the formulation of the medicinal active ingredient to the adhesive. In addition, because of the interaction between the active ingredient and adhesive the required storage stability of such a plaster cannot be met so that it cannot satisfy the strict governmental requirements for registration as a drug.

During prolonged storage under unfavorable conditions, the medicinal active ingredient frequently migrates into the adhesive, and, conversely, substituents of the adhesive migrate into the active ingredient formulation especially since an adhesive is not a chemically uniform substance but a mixture.

An object of the present invention is to provide a plaster which does not have the above-mentioned disadvantages of prior art plasters.

SUMMARY OF THE INVENTION

The invention accordingly relates to a self-adhesive plaster with separate medicinal active ingredient elements on a carrier coated with adhesive for transdermal application which is characterized in that there is a separating film element between each of the active ingredient elements and the layer of adhesive.

Each of the separating film elements preferably consists of a membrane which precludes the troublesome interactions between the medicinal active ingredient formulation and the layer of adhesive. The separating film elements are non-permeable. In a particularly suitable manner these separating film elements, for example of polyvinylidene chloride or copolymers thereof and also the active ingredient elements located on the film elements, are in each case applied as a dispersion with a high solids content by a printing press of the gravure printing type or in particular the screen printing type. As a result, according to the invention, no interaction can occur between the active ingredient and adhesive.

According to the invention it is not necessary when selecting the composition of the adhesive to take into consideration the medicinal active ingredient. The customary self-adhesive compositions can be used, in particular compositions of this type which do not irritate the skin, such as those based on an acrylate. If appropriate, adhesion promoters can be used to anchor the adhesive to the carrier web, the adhesion promoters being applied as a first coat to the carrier web.

If compositions which cross-link under the influence of electron beams are used as the adhesive compositions, the cross-linking is preferably carried out before the medicinal active ingredient formulation elements are applied to the elements of the separating film. This can be effected advantageously in steps, a coating of adhesive first being applied, as a dispersion, plastisol or organisol, to the carrier in a manner which is known per se and the elements of the separating film then being applied by the screen printing process after which cross-linking is carried out, and the active compound formulation is finally applied as a dispersion to the elements of the separating film by screen printing. It is advantageous for the separating film elements to have somewhat larger dimensions than the elements of the active ingredient to assure separation between the active ingredient elements and the adhesive.

Because the medicinal active ingredient and adhesive are isolated from each other, the adhesive can be any adhesive which is known per se and which does not irritate the skin and which can be processed as described above. Suitable adhesives are, inter alia, rubber, polyacrylic acid esters and polyisobutylene, if appropriate, together with tackifying resins. These adhesives are advantageously processed from aqueous, concentrated, thixotropic dispersions of adhesions, the solids content preferably being 55–65% by weight. Suitable examples are adhesives based on methyl acrylic acid esters with alkyl radicals of 4–18 carbon atoms, such as butyl acrylate, ethylhexyl acrylate or stearyl acrylate, cross-linked or noncross-linked, it being possible to effect cross-linking, if appropriate, by electron beam radiation.

The rotary screen printing process uses a rotating, weldless, drum-shaped and perforated rotary screen. In the inner jacket a mechanically or magnetically held round-edged or square doctor blade forces the dispersion into the drum through the perforations of the screen wall onto the carrier web. The carrier web passes the drum at a speed corresponding to the peripheral speed of the rotating screen drum driven by a back-pressure roller against the outer cover of the screen drum.

If electron beam cross-linking is to be carried out, this is advantageously effected after application of the adhesive and before application of the medicinal active ingredient.

The present invention may be used with any one of many different types of medications, such as those described in European Published Specification No. 72,251, including:
Antihypertensive agents
Antihypotensive agents
Vasodilators
β-Blockers
Calcium antagonists
Antiemetic agents
Antitussive agents
Sedatives
Analgesics
Psychotropic agents
Antiasthmatic agents
Antirheumatic agents
Antiarythmic agents
Antihistamines
Hormones
Antibiotics
Cytostatics The medicinal active ingredient formulation may contain film-forming auxiliary materials and other suitable pharmaceutical auxiliary materials which are suitable for fixing to the separating film elements and for optimum diffusion of the active ingredient into the skin.

Advantageously, the medicinal active ingredient elements are arranged in a regular pattern and have a diameter of up to about 5000 μm, usually 200–1500 μm. Preferably, the active ingredient elements have a diameter of up to about 600 μm and particularly 100–500 μm.

BRIEF DESCRIPTION OF THE DRAWINGS

The features and advantages of the present invention will become more clearly appreciated from the following description taken in conjunction with the accompanying drawings in which.

DETAILED DESCRIPTION OF THE PREFERRED EMBODIMENTS

Figure 1:
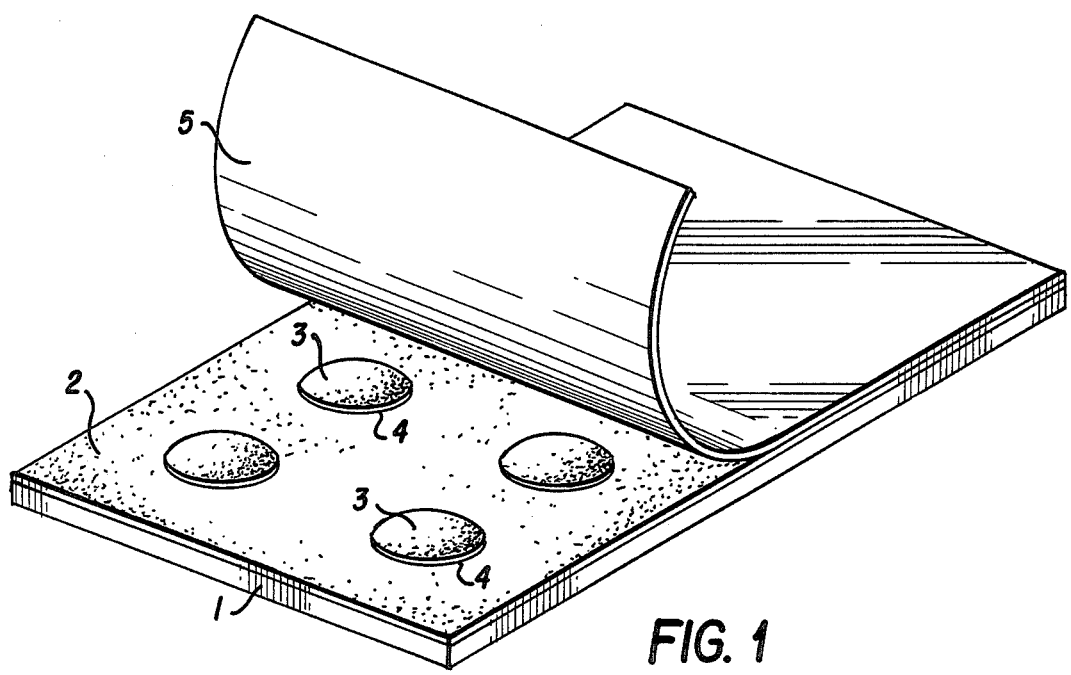
FIG. 1 is a perspective view of one embodiment of the plaster of the present invention.

FIG. 1 shows a carrier web 1 on which there is an adhesive layer 2. Individual separating film elements are in turn located in spaced relationship on the adhesive, and medicinal active ingredient elements 3 are located on respective film elements. These active ingredient elements are in turn protected with a releasable cover 5, the cover 5 being pulled off for use. The cover 5 preferably has an adhesive-repellent finish on the side facing the adhesive layer 2 if the cover 5 is not itself already adhesive-repellent.

Figure 2:
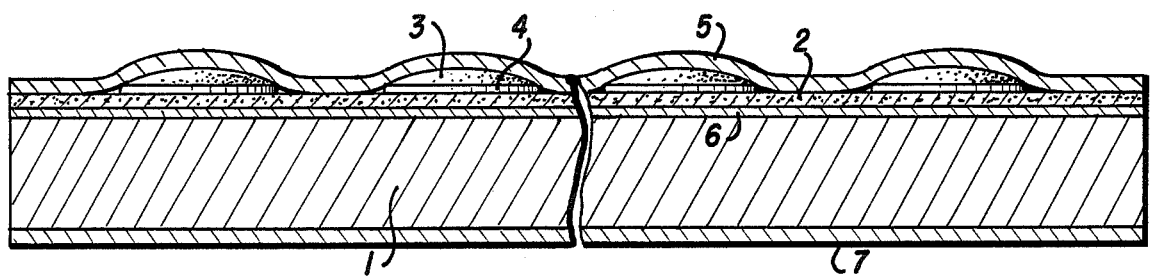
FIG. 2 is a cross-sectional view of a second embodiment of the plaster of the present invention.

In FIG. 2, showing an alternative form of the plaster, there is a layer of an adhesion promoter 6 between the carrier web 1 and the adhesive layer 2 for better anchoring of the adhesive to one side of the carrier web 1. There is a covering lacquer and/or a metal layer 7 produced by vapor deposition on the other side of the carrier 1. The medicinal active ingredient elements 3, separating film elements 4 and a releasable cover 5 are also shown.

The following is an example of a specific embodiment of the present invention:

EXAMPLE

A. Preparation of a medicinal active ingredient formulation 27.35 parts by weight of hydroxypropylmethylcellulose (Pharmacoat 603) are stirred into a cold mixture of 30 parts by weight of isopropanol, 30 parts by weight of water and 8.20 parts by weight of 1,2-propylene glycol. The mixture is warmed to 50° C. with continuous stirring until a clear solution has formed. 4.45 parts by weight of micronized 2-mehyl-4-chloro-6-methoxy-5-(2-imidazolin-2-yl)amino-pyramidine (Moxonidin) are carefully mixed into this solution.

B. Preparation of a separating film formulation 100 parts by weight of a commercially available aqueous polyvinylidene chloride dispersion (Diofan 190 D) are thickened to a viscosity of about 100 Pas by addition of 2 parts by weight of a 10% strength aqueous solution of the ammonium salt of a polyacrylic acid (Latekoll AS).

C. Preparation of the adhesive coated carrier web

A carrier web of a polyethylene terephthalate (Hostaphan RN 15) film 15 μm thick which, on one side, is aluminized and lacquered the color of skin, is coated over its entire surface with a self-adhesive composition so that the dry weight applied is about 35 g/m². An acrylic acid ester self-adhesive composition as described in German Patent Specification No. 2,743,979, for example, is particularly suitable.

D. Printing operation

The separating film formulation is applied to the dried and cross-linked self-adhesive layer with a first rotating screen printing unit at a web speed of 20 m/minute. A perforated cylinder which produces 200 elements per square centimeter, each of 500 μm base diameter, in regular arrangement may be used. The amount applied is regulated by adjustment of the doctor blade so that flat polyvinylidene chloride dispersion film elements which adhere firmly to the polyacrylate layer and, in the dried state, are about 20 μm thick are formed. Drying is carried out at about 70° C. in a warm-air drying canal 6 m in length.

A second rotating screen printing unit of the same type then prints the elements of medicinal active ingredient, each of 400 μm base diameter, onto the polyvinylidene chloride dispersion film elements such that they fit exactly. The amount applied is regulated via the doctor blade so that the cap-shaped elements are about 160 μm high in the dried state. This corresponds to an application amount of about 25 g of active ingredient formulation per m² of carrier web. This second printing unit is followed by another drying zone of the type described and then a laminating unit to apply the releasable cover.

E. Fabrication

The dried and covered web of material which has been printed twice can now be divided into individual plasters of any desired size, depending on the required dosage of active compound. If, for example, a size of 25 cm² is chosen, this surface has about 5000 elements of active ingredient corresponding to a content of 7 mg of 2-methyl-4-chloro-6-methoxy-5-(2-imidazolin-2-yl)-aminopyramidine (Moxonidin). These plasters are sealed individually into a diffusion-tight primary packing material, for example a flat bag of polyethylene/aluminum/paper laminated material.

It will be appreciated that various arrangements of the above-disclosed arrangement are possible without departing from the spirit of the present invention.

What is claimed is:

1. A self-adhesive medicinal plaster in which the medication is isolated from the adhesive, comprising:
   (a) a carrier web;
   (b) a continuous adhesive coating on one surface of said carrier web;
   (c) a plurality of non-permeable, separating film elements spaced from each other on the surface of said adhesive coating; in a predetermined pattern; and
   (d) a plurality of active ingredient elements containing at least one medication, each disposed on the surface of and within the perimeter of one of said separating film elements, said active ingredient elements each having a maximum surface dimension of about 5000 μm.

2. A self-adhesive medicinal plaster according to claim 1 further comprising a layer of adhesion promoter disposed between said carrier web and said adhesive coating.

3. A self-adhesive medicinal plaster according to claim 1 wherein the surface dimension of each of said active ingredient elements is between about 200 and 1500 μm.

4. A self-adhesive medicinal plaster according to claim 1 wherein the maximum surface dimension of each of said active ingredient elements is up to about 600 μm.

5. A self-adhesive medicinal plaster according to claim 4 wherein said non-permeable separating film elements are selected from the group consisting of polyvinylidene chloride, copolymers of polyvinylidene chloride and polyvinyl acetate.

6. a self-adhesive medicinal plaster according to claim 4 wherein only a single medicinal active ingredient element is disposed on each of said separating film elements.

7. A self-adhesive medicinal plaster according to claim 4 further comprising a removable cover web covering said surface of said adhesive coating including said separating film elements and medicinal active ingredient elements.

8. A self-adhesive medicinal plaster according to claim 4 further comprising a lacquer film covering the surface of said carrier web opposite said adhesive coating.

9. A self-adhesive medicinal plaster according to claim 8 further comprising a layer of adhesion promoter disposed between said carrier web and said adhesive coating.

10. A self-adhesive medicinal plaster according to claim 4 wherein a portion of said active ingredient elements comprise one type of medicinal composition and the remainder of said active ingredient elements comprise a different medicinal composition.

11. A self-adhesive medicinal plaster according to claim 4 wherein said medicinal active ingredient elements are arranged in a said predetermined pattern, each having a diameter of up to about 600 μm.

12. A self-adhesive medicinal plaster according to claim 4 wherein said medicinal active ingredient elements comprise 2-methyl-4-chloro-6-methoxy-5-(2-imidazolin-2-yl)amino-pyramidine.

13. A self-adhesive medicinal plaster according to claim 12 wherein the diameter of each of said medicinal active ingredient elements is between 100 and 500 μm.

14. A self-adhesive medicinal plaster according to claim 4 wherein the surface dimension of each of said active ingredient elements is between about 100 and 500 μm.

15. A method of making a self-adhesive plaster according to claim 4 wherein said step of applying, by a gravure printing process, a first dispersion of a film-forming material having a solids content on the surface of said adhesive coating comprises applying, by a gravure printing process, a dispersion of a polymer on the surface of said adhesive coating.

16. A method of making a self-adhesive plaster according to claim 15 wherein said polymer is selected from the group consisting of polyvinylidene chloride, copolymers of polyvinylidene chloride and polyvinyl acetate.

17. A self-adhesive medicinal plaster according to claim 1 wherein said non-permeable separating film elements are polymeric film elements.

18. A method of making a self-adhesive medicinal plaster in which the medication is isolated from the adhesive, comprising:
   (a) applying a continuous adhesive coating to one surface of a carrier web;
   (b) applying, by a gravure printing process, a first dispersion of a film-forming material having a high solids content on the surface of said adhesive coating at spaced locations in a predetermined pattern and drying said dispersion to form a plurality of non-permeable, separating film elements, spaced from each other on said surface of said adhesive coating; and
   (c) applying, by a gravure printing process, a second dispersion of at least one medication having a high solids content on the surface of each of said separating film elements and drying said dispersion to form a plurality of medicinal active ingredient elements containing at least one medication, each disposed on the surface of and within the perimeter of one of said separating film elements, each of said active ingredient elements having a maximum surface dimension of about 5000 μm.

19. A method of making a self-adhesive plaster according to claim 18 wherein said gravure printing processes are screen printing processes.

20. A method of making a self-adhesive plaster according to claim 18 wherein the amount of said second dispersion applied to the surface of each of said separating film elements by said gravure printing process provides one of said medicinal active ingredient elements having a surface dimension between about 200 and 1500 μm.

21. A method of making a self-adhesive plaster according to claim 18 wherein the amount of said second dispersion applied to the surface of each of said separating film elements by said gravure printing process provides one of said medicinal active ingredient elements having a maximum surface dimension of about 600 μm.

22. A method of making a self-adhesive plaster according to claim 18 wherein the amount of said second dispersion applied to the surface of each of said separating film elements by said gravure printing process provides one of said medicinal active ingredient elements having a maximum surface dimension between about 100 and 500 μm.

* * * * *